United States Patent [19]

Yabe et al.

[11] Patent Number: 4,670,586

[45] Date of Patent: Jun. 2, 1987

[54] METHOD FOR THE PRODUCTION OF α-ARYL-ALKANOIC ACID

[75] Inventors: Yuta Yabe, Kashiwa; Takamichi Watanabe, Mobara; Hisayuki Suzuki, Mobara, all of Japan

[73] Assignee: Nippon Chemicals Co., Ltd., Tokyo, Japan

[21] Appl. No.: 774,352

[22] Filed: Sep. 10, 1985

[30] Foreign Application Priority Data

Sep. 12, 1984 [JP] Japan .................................. 59-189636
Sep. 12, 1984 [JP] Japan .................................. 59-189637

[51] Int. Cl.$^4$ ............................................. C07C 65/11
[52] U.S. Cl. .................................... 562/466; 562/465; 562/496; 560/55; 560/56; 560/105
[58] Field of Search ................... 562/466, 465, 490; 560/55, 56, 105

[56] References Cited

U.S. PATENT DOCUMENTS

4,107,439 8/1978 Walker et al. .................... 560/55
4,142,054 2/1979 Amin et al. ...................... 560/105
4,414,405 11/1983 Giordano et al. ................. 560/105

FOREIGN PATENT DOCUMENTS

0034871 9/1981 European Pat. Off. ............ 562/466

OTHER PUBLICATIONS

J.O.C. 22, 662 (1957), Seven-Membered Cyclic Acetals.
JCS Chem. Com. No. 22 (1982), pp. 1311-1312, Reaction of 2-Alkyl-2-Phenyl-1,3-Dioxolans with Iodine Monochloride: Formation of Alpha-Phenylalkanoate Esters.
J.O.C. 21, 1366 (1956), Preparation and Properties of 1,3-Dioxep-5-enes.
Synthesis 23 (1974), Anteunis, Improved Direct Acetalization for (Strained) Cyclic Acetals.

Primary Examiner—Paul J. Killos
Attorney, Agent, or Firm—Gordon W. Hueschen

[57] ABSTRACT

A method for the production of an α-aryl-alkanoic acid represented by the general formula II:

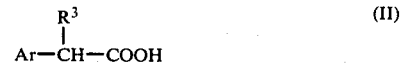

(II)

wherein $R^3$ stands for a hydrogen atom or an alkyl group and Ar for an aromatic residue, characterized by subjecting an α-haloalkyl-aryl ketal represented by the general formula I:

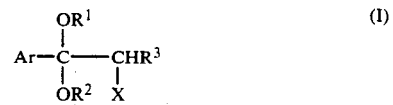

(I)

wherein Ar has the same meaning as defined above, $R^1$ and $R^2$ independently stand for an alkyl group and embrace the case wherein they jointly form a cyclic acetal, $R^3$ has the same meaning as defined above, and X stands for a halogen atom to a rearrangement reaction in the presence of at least one zinc compound selected from the group consisting of oxide, hydroxide, sulfide, carbonate, and basic carbonate of zinc and subsequently hydrolyzing the product of said rearrangement reaction.

18 Claims, No Drawings

METHOD FOR THE PRODUCTION OF α-ARYL-ALKANOIC ACID

BACKGROUND OF THE INVENTION

1. Field of the Invention

This invention relates to a method for the production of an α-aryl-alkanoic acid. More specifically, this invention relates to a method for the production of an α-aryl-alkanoic acid represented by the general formula II: Ar—CH($R^3$)COOH.

2. Description of Prior Art. Many of the compounds represented by the aforementioned general formula II show pharmacological actions. For example, α-(p-isobutylphenyl)-propionic acid, the species having a p-isobutyl phenyl group as Ar and a methyl group as $R^3$, is Ibuprofen, a compound useful as antiphlogistics, analgesic, and antipyretics. Numerous attempts have been made to date to obtain α-aryl-ethanoic acid represented by the general formula IV, Ar—CH(CH$_3$)—COOH, from an arylethyl ketone represented by the general formula III, Ar—CO—CH$_2$CH$_3$. Typical examples are as follows.

U.S. Pat. Nos. 4,142,054, 4,107,439 and G.B. Pat. No. 1,535,690A:

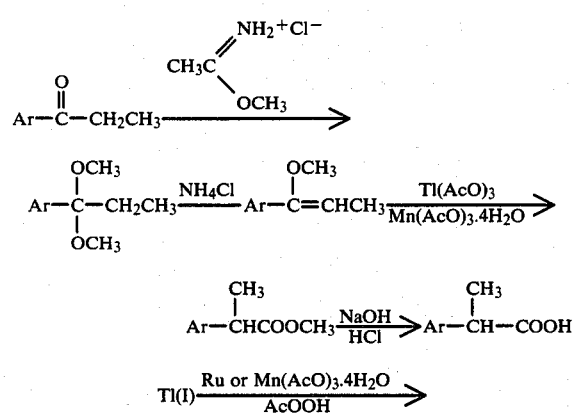

To be used cyclically as Tl (III).

This method uses an expensive and highly toxic thallium (III) salt and, therefore, requires meticulous care to be directed to preventing thallium from mingling into the product intended as a medicine, rendering it inevitable to increase the number of steps involved in the production. The method further uses an expensive raw material, i.e. acetiminoether hydrochloride, and proves disadvantageous from the economic point of view.

(2) K. Fujii et al: Synthesis, 444 (1983):

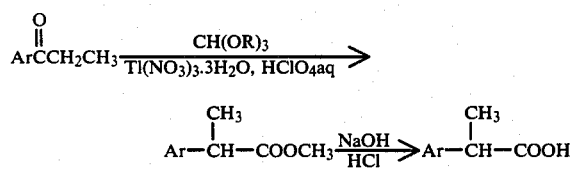

This method also uses the highly toxic thallium (III) salt and, therefore, requires meticulous care to be directed to preventing thallium from mingling into the product intended as a medicine. It further uses an expensive trialkyl ester of ortho-formic acid and proves expensive.

(3) Andre Goosen et al: J. chem. Soc., Commun., 1311–1312 (1982):

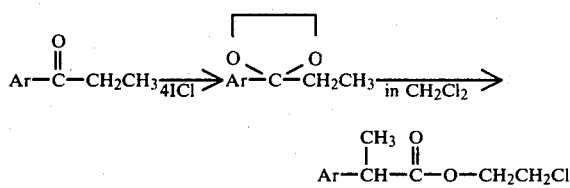

This method turns out to be an expensive approach because it is required to use as much as 4 mols of expensive ICl on an alkyl-aryl dioxolane which is obtained as an intermediate.

(4) E.P. Pat. No. 48,136A:

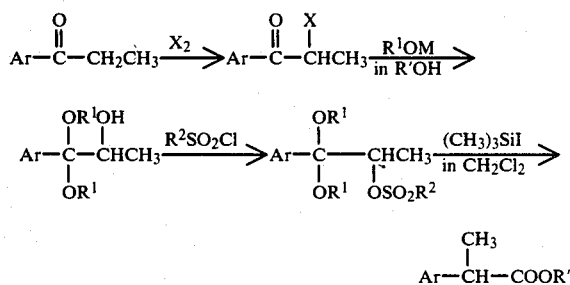

This method is uneconomical and expensive because it involved a complicated and highly roundabout procedure consisting of many steps.

(5) E.P. Pat. No. 34,871A and U.S. Pat. No. 4,414,405:

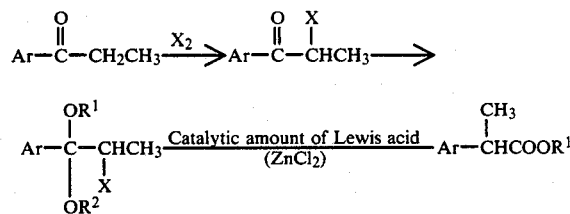

Although this method uses a halogenide or a sulfate of metal as the Lewis acid, it is required to carry out the reaction mainly in a nonpolar medium under an anhydrous condition. Among the catalysts effective at all in the reaction, those which are particularly effective turn out to be harmful metal salts. Since the reactants are highly corrosive, this method entails an expensive operation. This method also has the disadvantage that the refinement of the product requires meticulous care.

(6) E.P. Pat. No. 101,124A:

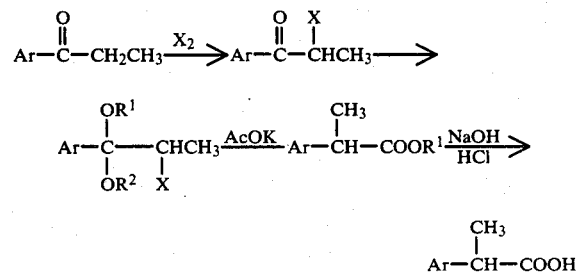

This method carries out the reaction mainly in the presence of a weakly basic compound such as an organic amine or an alkali or alkaline earth metal salt and, consequently, limits the medium for the reaction to a polar protonic solvent such as an aqueous alcohol or glycol. The catalyst is required to be used at least in an equimolar amount relative to the acetal. The method, as evaluated by repeating the procedures of working examples cited in the specification, is found to have the disadvantage that the reaction velocity is low and the yield is also low.

An object of this invention, therefore, is to provide a novel method for the production of an α-aryl-alkanoic acid.

Another object of this invention is to provide a method for producing an α-aryl-alkanoic acid in a high yield by using a safe and inexpensive catalyst instead of either using any of the expensive catalysts and raw materials necessary for the conventional methods or using a toxic catalyst or a chemical liable to explode.

Yet another object of this invention is to provide a method for the production of an α-aryl-alkanoic acid by a very simple procedure.

SUMMARY OF THE INVENTION

The objects described above are accomplished by a method for the production of an α-aryl-alkanoic acid represented by the general formula II:

(II)

wherein $R^3$ stands for a hydrogen atom or an alkyl group and Ar for an aromatic residue, characterized by subjecting an α-haloalkyl-aryl ketal represented by the general formula I:

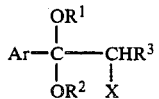

(I)

wherein Ar has the same meaning as describd above, $R^1$ and $R^2$ independently stand for an alkyl group and embrace the case wherein they jointly form a cyclic acetal, $R^3$ has the same meaning as described above, and X stands for a halogen atom to a rearrangement reaction in the presence of at least one zinc compound selected from the group consisting of oxide, hydroxide, sulfide, carbonate, and basic carbonate of zinc and subsequently hydrolyzing the resultant product of said rearrangement reaction

DESCRIPTION OF PREFERRED EMBODIMENT

The symbol Ar in the aforementioned general formulas I and II represents an aromatic residue. Desirably, this aromatic residue is phenyl substituted by one or two substituents selected from the class consisting of alkyl of 1 to 6 carbon atoms, alkoxy of 1 to 4 carbon atoms, and alkenyloxy, phenyl, and phenoxy of 2 to 4 carbon atoms or naphthyl substituted by one or two alkoxys of 1 to 4 carbon atoms. Particularly desirably the aromatic residue is phenyl substituted by one or two substituents selected from the class consisting of alkyl of 1 to 4 carbon atoms, alkoxy of 1 or 2 carbon atoms, and alkenyloxy, phenyl, and phenoxy of 2 to 4 carbon atoms or naphthyl substituted by one or two alkoxy of 1 to 2 carbon atoms.

In the general formula I, $R^1$ and $R^2$ independently stand for a saturated or unsaturated straight or branched alkyl of 1 to 12, preferably 1 to 4, carbon atoms or jointly form a saturated or unsaturated straight or branched alkyl of 2 to 12, preferably 2 to 4, carbon atoms. $R^1$ and $R^2$, when joined to each other, form a 5- to 7-member oxygen-containing heterocycle.

In the general formula I, X stands for a halogen atom, preferably a chlorine atom or bromine atom, and particularly desirably a bromine atom.

In the general formulas I and II, $R^3$ stands for a hydrogen atom, an alkyl of 1 to 6, preferably 1 or 2, carbon atoms, or a cycloalkyl of 3 to 7, preferably 5 or 6 carbon atoms.

As typical examples of the α-haloalkyl-aryl ketal of the general formula I to be used as the starting material, the following compounds disclosed in E.P. Pat. No. 34,871A and U.S. Pat. No. 4,414,405, for instance, may be cited.

2-Bromo-1,1-dimethoxy-1-(4'-isobutylphenyl)-propane,
2-bromo-1,1-dimethoxy-1-(6'-methoxy-2'-naphthyl)-propane,
2-chloro-1,1-dimethoxy-1-(6'-methoxy-2'-naphthyl)-propane,
2-bromo-1,1-diethoxy-1-(6'-methoxy-2'-naphthyl)-propane,
2-bromo-1-(6'-methoxy-2'-naphthyl)-1-one,
2-(1'-bromoethyl)-2-(6'-methoxy-2'-naphthyl)-1,3-dioxolane,
2-(1'-bromoethyl)-2-(6'-methoxy-2'-naphthyl)-4,5,-dimethyl-1,3-dioxolane,
2-(1'-bromoethyl)-2-(5'-bromo-6'-methoxy-2'-naphthyl)-1,3-dioxolane,
2-(1'-bromoethyl)-2-(4'-isobutylphenyl)-1,3-dioxolane,
2-(1'-chloroethyl)-2-(4'-isobutylphenyl)-1,3-dioxolane,
2-(1'-bromoethyl)-2-(4'-isobutylphenyl)-1,3-dioxolane, and
2-bromo-1-(4'-isobutylphenyl)-1,1-dimethoxypropane.

These α-haloalkyl-aryl-ketals are compounds which are easily obtained by acetalizing α-haloalkyl-aryl ketones by the method described as in J. Org. Chem., 21, 1366 (1956), J. Org. Chem., 22, 662 (1957), Synthesis 23 (1974), E.P. Pat. No. 34,871A and U.S. Pat. No. 4,414,405, for example.

The zinc compound to be used as the catalyst in this invention is selected from the group consisting of oxide, hydroxide, sulfide, carbonate, and basic carbonate of zinc. Just one zinc compound or a mixture of two or more zinc compounds selected from this group can be used. Among those oxide and hydroxide of zinc are desirable, oxide thereof is particularly desirable. Typical examples of the aforementioned zinc compound are ZnO, Zn(OH)$_2$, ZnS, ZnCO$_3$, and 2ZnCO$_3$·3Zn(OH)$_2$. Although the amount of the catalyst to be used is not specifically defined, it is desired to fall in the range of 0.001 to 5 mols, more desirably 0.01 to 2 mol, most desirably 0.1 to 1 mol, per mol the α-haloalkylaryl ketal represented by the aforementioned general formula I.

In this invention, it is desirable to carry out the rearrangement reaction in the presence of a diluent. Examples of the diluent usable for the rearrangement reaction include aliphatic and aromatic halogenated hydrocarbons such as chloroform, methylene chloride, carbon tetrachloride, methyl bromide, dichloroethane, trichloroethane, tetrachloroethylene, monochlorobenzene, and dichlorobenzene; aliphatic, alicyclic, and aromatic hydrocarbons such as hexane, octane, cyclohexane, benzene, toluene, and xylene; dioxane; ethers such as alkylene glycol monoalkyl ethers (such as alkylenes of 2 to 4 carbon atoms and alkyls of 1 to 4 carbon atoms) and diethyl ether; esters such as alkyl (such as, for example, methyl and ethyl) acetates, alkyl (such as, for example, methyl and ethyl) ortho-formates and alkyl (such as, for example, methyl and ethyl) ortho-acetates; ketones such as acetone and methylethyl ketone: and polyhydric alcohols such as ethylene glycol, diethylene glycol, triethylene glycol, tetraethylene glycol, propylene glycol, trimethylene glycol, dipropylene glycol, tripropylene glycol, 1,2-butane diol, 1,3-butane diol, 1,4-butane diol, 1,5-hexane diol, 2,3-butane diol, 1,4-pentane diol, 1,5-pentane diol, 2,4-pentane diol, 1,6-hexane diol, 2,5-hexane diol, 1,7-heptane diol, 1,8-octane diol, 1,9-nonane diol, 1,10-decane diol, neopentyl glycol, glycerin, 1,2,3-hexane triol, and pentaerythritol, for example. Among the polyhydric alcohols cited above, ethylene glycol, propylene glycol and diethylene glycol are particularly desirable. When required just one diluent or a mixture of two diluents selected from the group enumerated above can be used. Although the amount of the diluent to be used is not specifially defined, it is generally desired to fall in the range of 0.01 to 100 parts by weight, preferably 0.1 to 100 parts by weight, and most preferably, 1 to 10 parts by weight per one part by weight of the compound of the aforementioned general formula 1.

In accordance with this invention, the rearrangement reaction of the compound of the aforementioned general formula I proceeds at a high speed and the catalyst causes virtually no discernible corrosion of the equipment and, after completion of the reaction, the catalyst can be recovered in a solid state and put to use repetitively. The fact that the otherwise inevitable disposal of spent catalyst is avoided renders the method highly advantageous from the economic point of view.

The rearrangement reaction of the compound of the general formula I by the method of this invention proceeds advantageously at a temperature in the range of 0° C. to 250° C., preferably 100° to 200° C. The reaction time is in the range of 1 to 48 hours, preferably 3 to 16 hours.

The method of this invention comprises first mixing an α-haloalkyl-aryl ketal with one catalyst or a mixture of two or more catalysts selected from the aforementioned group and the aforementioned diluent, keeping the resultant mixture at a temperature in the aforementioned range for the aforementioned reaction time, thereby completing the rearrangement reaction of the α-haloakyl-aryl ketal, then removing the catalyst from the reaction mixture by filtration, distilling the reaction mixture thereby expelling the diluent, and hydrolyzing the residue by the conventional method thereby producing an α-aryl-alkanoic acid.

Now, the present invention will be described more specifically below with reference to working examples. It should be noted that this invention is not limited to the examples.

EXAMPLE 1

In a reactor, 3.2 g (0.01 mol) of 2-(1'-bromoethyl)-2-(4'-isobutylphenyl)-1,3-dioxolane, 0.405 g (0.005 mol) of zinc oxide, and 15 ml of toluene were refluxed under application of heat for eight hours. The reaction mixture was filtered to remove the catalyst and then distilled to expel the toluene. The resultant residue and 15 ml of methanol and 30 ml of an aqueous solution containing sodium hydroxide in a concentration of 50% by weight added thereto were refluxed for four hours. The reaction mixture which resulted was poured into 50 ml of water. The aqueous solution consequently obtained was acidified with concentrated hydrochloric acid and then extracted twice, each from 40 ml of toluene. Then, the extract was distilled to expel the toluene. Consequently, there was 1.7 g (0.008 mol) of 2-(4'-isobutylpheny)-propionic acid. This product represented a yield of 83% and had a melting point of 76° to 77° C.

EXAMPLES 2-8

Various α-haloalkyl-aryl ketals were subjected to rearrangement reaction by following the procedure of Example 1, except that various solvents and catalysts shown in Table 1 were used and various conditions indicated in the same table were adopted. The products of the rearrangement reaction were subjected to hydrolysis by following the same procedure. The results are shown in Table 1.

TABLE 1

| Example | α-Haloalkyl-aryl ketal (mol) | Catalyst (mol) | Diluent (ml) | Reaction Temperature (°C.) | Reaction Time (hr) | Yield of α-aryl-alkanoic acid (%) |
|---|---|---|---|---|---|---|
| 2 | 2-(1'-Bromoethyl)-2-(4'-isobutylphenyl)-1,3-dioxolane (0.01) | Zn(OH)₂ (0.005) | toluene (15) | 118 | 16 | 83 |
| 3 | 2-(1'-Bromoethyl)-2-(4'-isobutylphenyl)-1,3-dioxolane (0.01) | 2ZnCO₃.3Zn(OH)₂ (0.001) | toluene (15) | 118 | 10 | 74 |
| 4 | 2-(1'-Bromoethyl)-2-(4'-isobutylphenyl)-1,3-dioxolane (0.01) | ZnS (0.005) | toluene (15) | 118 | 8 | 77 |
| 5 | 2-Bromo-1-(4'-isobutylphenyl)-1,1-dimethoxypropane (0.01) | ZnO (0.005) | xylene (15) | 143 | 6 | 92 |
| 6 | 2-(1'-Bromoethyl)-2-(4'-isobutylphenyl)-1,3-dioxolane (0.01) | Zn(OH)₂ (0.005) | xylene (15) | 143 | 13 | 84 |
| 7 | 2-(1'-Bromoethyl)-2-(4'-isobutylphenyl)-1,3-dioxolane (0.01) | ZnO (0.005) | monochlorobenzene(15) | 132 | 7 | 90 |
| 8 | 2-Bromo-1-(6'-methoxy-2'-naphthyl)-propane-1-one(0.01) | ZnO (0.005) | toluene (15) | 118 | 4 | 95 |

EXAMPLE 9

The reaction procedure of Example 1 was repeated by using as the catalyst the zinc oxide recovered by filtration from the reaction mixture obtained by following the procedure of Example 1. Consequently, 2-(4'-isobutylphenyl)-propionic acid was obtained in a yield of 90%. This acid showed a melting point of 76° to 77°.

EXAMPLE 10

In a reactor, 3.2 g (0.01 mol) of 2-(1'-bromoethyl)-2-(4'-isobutylphenyl)-1,3-dioxolane and 0.081 g (0.001 mol) of zinc oxide were heated for reaction at 140° for two hours. The resultant reaction mixture was filtered to remove the catalyst. The filtrate and 15 ml of methanol and 40 ml of an aqueous solution containing sodium hydroxide in a concentration of 50% by weight added thereto were refluxed under application of heat for four hours. The resultant reaction mixture was poured into 50 ml of water. The aqueous solution so produced was acidified with concentrated hydrochloric acid and then extracted twice, each from 40 ml of toluene. Then, the extract was distilled to expel the toluene. Consequently, there was obtained 1.86 g (0.0875 mol) of 2-(4'-isobutylphenyl)-propionic acid. This product represented a yield of 88% and showed a melting point of 76° C. to 77° C.

EXAMPLE 11-18

Various α-haloalkyl-aryl ketals were subjected to rearrangement reaction by following the procedure of Example 10, except that various solvents and catalysts shown in Table 2 were used and various conditions indicated in the same table were adopted. The products of the rearrangement reaction were subjected to hydrolysis again by following the procedure of Example 10. The results are shown in Table 2.

zinc oxide, and 40 ml of monochlorobenzene were heated at 140° C. for two hours. The resultant reaction mixture was filtered to recover the catalyst (93%) and then distilled to expel the monochlorobenzene. Then, the residue was subjected to hydrolysis by following the procedure of Example 10 (150 ml of methanol and 400 ml of 50% NaOH aqueous solution). Consequently, there was obtained 2-(4'-isobutylphenyl)-propionic acid in a yield of 99%. When the same reaction was repeated by using the recovered zinc oxide as the catalyst, there was obtained 2-(4'-isobutylphenyl)-propionic acid in a yield of 95%.

EXAMPLE 20

In a reactor, 3.2 g (0.01 mol) of 2-(1'-bromoethyl)-2-(4'-isobutylphenyl)-1,3-dioxolane, 0.081 g (0.001 mol) of zinc oxide, and 15 ml of ethylene glycol were refluxed under application of heat for four hours. The resultant reaction mixture and 30 ml of an aqueous solution containing sodium hydroxide in a concentration of 50% by weight added thereto were refluxed under application of heat for four hours. The resultant aqueous solution was acidified with concentrated hydrochloric acid and then extracted twice, each from 40 ml of toluene. Then, the extract was distilled to expel the toluene. Consequently, there was obtained 1.7 g (0.008 mol) of 2-(4'-isobutylphenyl)-propionic acid. This product represented a yield of 83% and showed a melting point of 76° to 77° C.

EXAMPLE 21-27

Various α-haloalkyl-aryl ketals were subjected to rearrangement reaction by following the procedure of Example 20, except that various solvents and catalysts shown in Table 3 were used and various conditions indicated in the same table were adopted. The products of this reaction were subjected to hydrolysis again by

TABLE 2

| Example | α-Haloalkyl-aryl ketal (mol) | Catalyst (mol) | Diluent (ml) | Reaction Temperature (°C.) | Reaction Time (hr) | Yield of α-aryl-alkanoic acid* (%) |
|---|---|---|---|---|---|---|
| 10 | 2-(1'-Bromoethyl)-2-(4'-isobutylphenyl)-1,3-dioxolane (0.01) | ZnO (0.001) | none | 140 | 2 | 88 |
| 11 | 2-(1'Bromoethyl)-2-(4'-isobutylphenyl)-1,3-dioxolane (0.01) | ZnO (0.001) | toluene (4) | 128 | 2 | 97 |
| 12 | 2-(1'-Bromoethyl)-2-(4'-isobutylphenyl)-1,3-dioxolane (0.01) | ZnO (0.001) | xylene (4) | 140 | 2 | 88 |
| 13 | 2-(1'-Bromoethyl)-2-(4'-isobutylphenyl)-1,3-dioxolane (0.01) | ZnO (0.001) | monochloro-benzene(4) | 140 | 2 | 99 |
| 14 | 2-(1'-Bromoethyl)-2-(4'-isobutylphenyl)-1,3-dioxolane (0.01) | Zn(OH)$_2$ (0.005) | toluene (4) | 128 | 2 | 83 |
| 15 | 2-(1'-Bromoethyl)-2-(4'-isobutylphenyl)-1,3-dioxolane (0.01) | 2ZnCO$_3$.3Zn(OH)$_2$ (0.001) | toluene (4) | 128 | 3 | 74 |
| 16 | 2-(1'Bromoethyl)-2-(4'-isobutylphenyl)-1,3-dioxolane (0.01) | ZnS (0.01) | toluene (4) | 128 | 2 | 77 |
| 17 | 2-Bromo-1-(4'-isobutylpheny)-1,1-dimethoxypropane (0.01) | ZnO (0.001) | toluene (4) | 128 | 2 | 92 |
| 18 | 2-Bromo-1-(6'-methoxy-2'-naphthyl)-propane-1-one(0.01) | ZnO (0.001) | toluene (4) | 128 | 2 | 95 |

*2-(4'-Isobutylphenyl)-propionic acid in Examples 10–17.
2-(6'-Methoxy-2'-naphthyl)-propionic acid in Example 18.

EXAMPLE 19

In a reactor, 32 g (0.10 mol) of 2-(1'-bromoethyl)-2-(4'-isobutylphenyl)-1,3-dioxolane, 0,81 g (0.01 mol) of following the procedure of Example 20. The results are shown in Table 3.

TABLE 3

| Example | α-Haloalkyl-aryl ketal (mol) | Catalyst (mol) | Diluent (ml) | Reaction Temperature (°C.) | Reaction Time (hr) | Yield of α-aryl-alkanoic acid (%) |
|---|---|---|---|---|---|---|
| 21 | 2-(1'-Bromoethyl)-2-(4'-isobutylphenyl)-1,3-dioxolane (0.01) | ZnO (0.001) | PG* (15) | 175 | 4 | 91 |
| 22 | 2-(1'-Bromoethyl)-2-(4'-isobutylphenyl)-1,3-dioxolane (0.01) | ZnO (0.001) | EG** (15) | 175 | 4 | 92 |
| 23 | 2-(1'-Bromoethyl)-2-(4'-isobutylphenyl)-1,3-dioxoxlane (0.01) | Zn(OH)$_2$ (0.001) | PG (15) | 175 | 4 | 91 |
| 24 | 2-(1'-Bromoethyl)-2-(4'-isobutylphenyl)-1,3-dioxolane (0.01) | 2ZnCO$_3$.3Zn(OH)$_2$ (0.001) | DEG*** (15) | 175 | 4 | 90 |
| 25 | 2-(1'-Bromoethyl)-2-(4'-isobutylphenyl)-1,3-dioxolane (0.01) | ZnS (0.001) | PG (15) | 175 | 4 | 88 |
| 26 | 2-Bromo-1-(4'-isobutylphenyl)-1,1-dimethoxypropane (0.01) | ZnO (0.001) | EG (15) | 175 | 4 | 90 |
| 27 | 2-Bromo-1-(6'-methoxy-2'-naphthyl)-propane-1-one(0.01) | ZnO (0.001) | EG (15) | 175 | 4 | 94 |

*PG: Propylene glycol
**EG: Ethylene glycol
***DEG: Diethylene glycol

EXAMPLE 28

The reaction procedure of Example 20 was repeated by using as the catalyst the zinc oxide recovered from the reaction solution obtained by the procedure of Example 20. Consequently, 2-(4'-isobutylphenyl)-propionic acid was obtained in a yield of 92%. This product showed a melting point of 76° to 77° C.

As described above, the method of this invention uses the aforementioned zinc compound as the catalyst for the rearrangement reaction of an α-haloalkyl-aryl ketal. Thus, it is capable of producing an α-aryl-alkanoic acid by a very simple procedure using the safe and inexpensive catalyst instead of either using any of the expensive catalysts and raw materials necessary for the conventional methods or using any toxic catalyst or a chemical susceptible of explosion. The fact that the zinc compound normally recognized neither as Lewis acid nor as weakly basic compound is highly effective in the aforementioned rearrangement reaction has surpassed all expectations. It is widely known that Lewis acids, particularly metal halides, cause serious corrosion of equipment. The specific catalyst used in the method of this invention is found to cause virtually no discernible corrosion of the equipment.

What is claimed is:

1. A method for the production of an α-aryl-alkanoic acid represented by the general fomrula II:

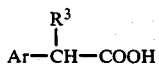

(II)

wherein $R^3$ stands for a hydrogen atom or an alkyl group and Ar for an aromatic residue, characterized by subjecting an α-haloalkyl-aryl ketal represented by the general formula I:

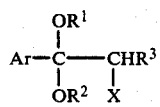

(I)

wherein Ar has the same meaning as defined above, $R^1$ and $R^2$ independently stand for an alkyl group and embrace the case wherein they jointly form a cyclic acetal, $R^3$ has the same meaning as defined above, and X stands for a halogen atom to a rearrangement reaction in the presence of at least one zinc compound selected from the group consisting of oxide, hydroxide, sulfide, carbonate, and basic carbonate of zinc without the addition of organic or inorganic acid and subsequently hydrolyzing the product of said rearrangement reaction.

2. A method according to claim 1, wherein said zinc compound is an oxide or a hydroxide of zinc.

3. A method according to claim 1, wherein said zinc compound is an oxide of zinc.

4. A method according to claim 1, wherein said rearrangement reaction of an α-haloalkyl-aryl ketal is carried out in the presence of a diluent.

5. A method according to claim 4, wherein said diluent is an aliphatic, alicyclic, or aromatic hydrocarbon or an aliphatic or aromatic halogenated hydrocarbon.

6. A method according to claim 4, wherein said diluent is a polyhydric alcohol of 2 to 12 carbon atoms.

7. A method according to claim 6, wherein said polyhydric alcohol is a divalent alcohol.

8. A method according to claim 7, wherein said divalent alcohol has 2 to 4 carbon atoms.

9. A method according to claim 8, wherein said divalent alcohol is ethylene glycol, propylene glycol, or diethylene glycol.

10. A method according to claim 1, wherein said zinc compound is used in an amount of 0.001 to 5 mols per mol of said α-haloalkyl-aryl ketal.

11. A method according to claim 1, wherein said zinc compound is used in an amount of 0.01 to 2 mols per mol of said α-haloalkyl-aryl ketal.

12. A method according to claim 4, wherein said zinc diluent is used in an amount of 0.01 to 100 parts by weight per part by weight of said α-haloalkyl-aryl ketal.

13. A method according to claim 5, wherein said diluent is used in an amount of 0.1 to 100 parts by weight per part by weight of said α-haloalkyl-aryl ketal.

14. A method according to claim 6, wherein said diluent is used in an amount of 0.1 to 10 parts by weight per part by weight of said α-haloalkyl-aryl ketal.

15. A method according to claim 1, wherein said rearrangement reaction is carried out at a temperature in the range of 0° to 250° C.

16. A method according to claim 1, wherein said rearrangement reaction is carried out at a temperature in the range of 100° to 200° C.

17. A method according to claim 1, wherein said substituent Ar is a phenyl substituted by one or two substituents selected from the class consisting of alkyls of 1 to 6 carbon atoms, alkoxys of 1 to 4 carbon atoms, and alkenyloxys, phenyls, and phenoxys of 2 to 4 carbon atoms or a naphthyl substituted by one or two alkoxys of 1 to 4 carbon atoms.

18. A method according to claim 1, wherein $R^1$ and $R^2$ independently stand for a saturated or unsaturated alkyl.

* * * * *

UNITED STATES PATENT AND TRADEMARK OFFICE
CERTIFICATE OF CORRECTION

PATENT NO.  : 4,670,586
DATED       : June 2, 1987
INVENTOR(S) : Yuta Yabe, Takamichi Watanabe and Hisayuki Suzuki It is certified that error appears in the above-identified patent and that said Letters Patent is hereby corrected as shown below:

Col. 1, line 13; begin a new paragraph with "Many"
Col. 1, lines 21&22; "Ar—CH(CH$_3$)—COOH" should read -- Ar—CH(CH$_3$)—COOH --
Col. 2, approximately line 7; below the first arrow in the formula, "4ICI" should be deleted and re-inserted above the second arrow in that same formula.
Col. 2, approximately line 23, in the formula; "OR $^1$OH" should read -- OR$^1$ OH --
Col. 4, line 29; "naphthyl)-1-one," should read -- naphthyl)-propane-1-one, --
Col. 12, line 8; "claim 1," should read -- claim 17, --

Signed and Sealed this

Tenth Day of May, 1988

*Attest:*

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. : 4,670,586

DATED : June 2, 1987

INVENTOR(S) : Yuta Yabe, Takamichi Watanabe and Hisayuki Suzuki

It is certified that error appears in the above-identified patent and that said Letters Patent is hereby corrected as shown below:

Title Page, [73] Assignee:; "Nippon" should read -- Nippoh --

Signed and Sealed this

Eighteenth Day of January, 1994

Attest:

BRUCE LEHMAN

Attesting Officer   Commissioner of Patents and Trademarks